United States Patent [19]
Sioshansi et al.

[11] Patent Number: 6,030,333
[45] Date of Patent: Feb. 29, 2000

[54] IMPLANTABLE RADIOTHERAPY DEVICE

[75] Inventors: Piran Sioshansi, Lincoln; Raymond J. Bricault, West Boylston, both of Mass.

[73] Assignee: RadioMed Corporation, Billerica, Mass.

[21] Appl. No.: 08/956,863

[22] Filed: Oct. 24, 1997

[51] Int. Cl.$^7$ ................................................. A61N 5/00
[52] U.S. Cl. ................................................................. 600/3
[58] Field of Search ............................. 600/1–8; 128/898

[56] References Cited

U.S. PATENT DOCUMENTS

| | | | |
|---|---|---|---|
| 5,059,166 | 10/1991 | Fischell et al. | 600/3 |
| 5,176,617 | 1/1993 | Fischell et al. | 600/3 |
| 5,342,283 | 8/1994 | Good | 600/8 |
| 5,607,442 | 3/1997 | Fischell et al. | 600/3 |
| 5,725,572 | 3/1998 | Lam et al. | 600/3 X |
| 5,871,436 | 2/1999 | Eury | 600/3 |

FOREIGN PATENT DOCUMENTS 799 189   8/1983   U.S.S.R. .

OTHER PUBLICATIONS

Blasko, "Long–Term Outcomes Of External Beam Irradiation And 1–25/:Pd–103 Brachytherapy Boost For Prostate Cancer", *I. J. Radiation Oncology ● Biology ● Physics*, vol. 36, No. 1, Supplemental 1996.

Dattoli et al., "$^{103}$Pd Brachytherapy and External Beam Irradiation For Clinically Localized, High–Risk Prostatic Carcinoma", *Int. J. Radiation Oncology Biol. Phys.*, vol. 35, No. 5, pp. 875–879, 1996.

Finger et al., "Palladium 103 Ophthalmic Plaque Radiotherapy", *Arch Ophthalmol*, vol. 109, pp. 1610–1613, 1991.

Finger et al., "Palladium–103 Versus Iodine–125 For Ophthalmic Plaque Radiotherapy", *Int. J. Radiation Oncology Biol. Phys.*, vol. 27, No. 4, pp. 849–854, 1993.

Fix, PD–103 Seeds Treat Introacular Tumors With Less Radiation Exposure To Healthy Tissue, *ADVANCE For Administrators in Radiology*, p. 47, Sep. 1994.

Guttman, "Interstitpal Brachytherapy Making Comeback", *Urology Times*, Oct. 1993.

Prestidge et al., "Post–Treatment Biopsy Results Following Interstitial Brachytherapy In Early Stage Prostate Cancer", 37th Annual Scientific Meetings of the American Society For Therapeutic Radiology and Oncology, Miami Beach, Florida, Oct. 9, 1995.

Ragde, "Brachytherapy (Seed Implantation) for Clinically Localized Prostate Cancer", *J. Surg. Oncol.*, vol. 64, pp. 79–81, 1997.

Ragde et al., "Brachytherapy In The Management Of Clinically Organ–Confined Prostate Cancer", First International Consultation on Prostate Cancer, World Health Organization, Monacao, Jun. 20–22, pp. 1–12, 1996.

Skerrett, "Radioactive Pellets Speed Prostate Recovery", *Medical World News*, Jan. 1994.

Skolnick, "Radiation Therapy For "Wet" Type Macular Degeneration Shows Promise In Early Trials", *JAMA*, vol. 277(9) 1997.

"Therapeutic Options Available For Treating Prostate Cancer", *The BBI Newsletter*, vol. 19, No. 4, pp. 72–74, Apr. 1996.

"TheraSeed™ Palladium 103 Implants", *Theragents Corporation*. May 1990.

"Beta Radiation May Stop Wet Macular Degeneration", *eyesotopes*, The International Newsletter For Eye Tumor Experts, No. 5, Apr. 1997.

*Primary Examiner*—Samuel Gilbert
*Attorney, Agent, or Firm*—McDermott, Will & Emery

[57] ABSTRACT

A general purpose implantable radiotherapy device for delivering a predetermined dose of radiation in a predetermined radiation pattern. The device includes a biocompatible template adapted for implantation at a treatment site in a patient, and one or more radiation sources which are incorporated directly into at least a portion of the template, preferably by ion implantation methods. The shape of the radiation pattern from the device is determined at least in part by the location and distribution of the radiation source or sources incorporated into the template, and not solely by the shape of the template. The device is suitable for a wide variety of radiotherapy applications.

55 Claims, 4 Drawing Sheets

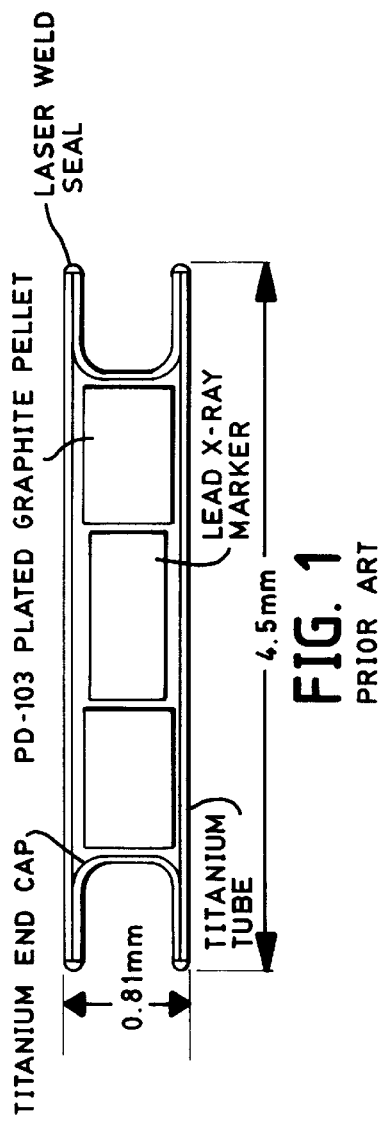
FIG. 1
PRIOR ART
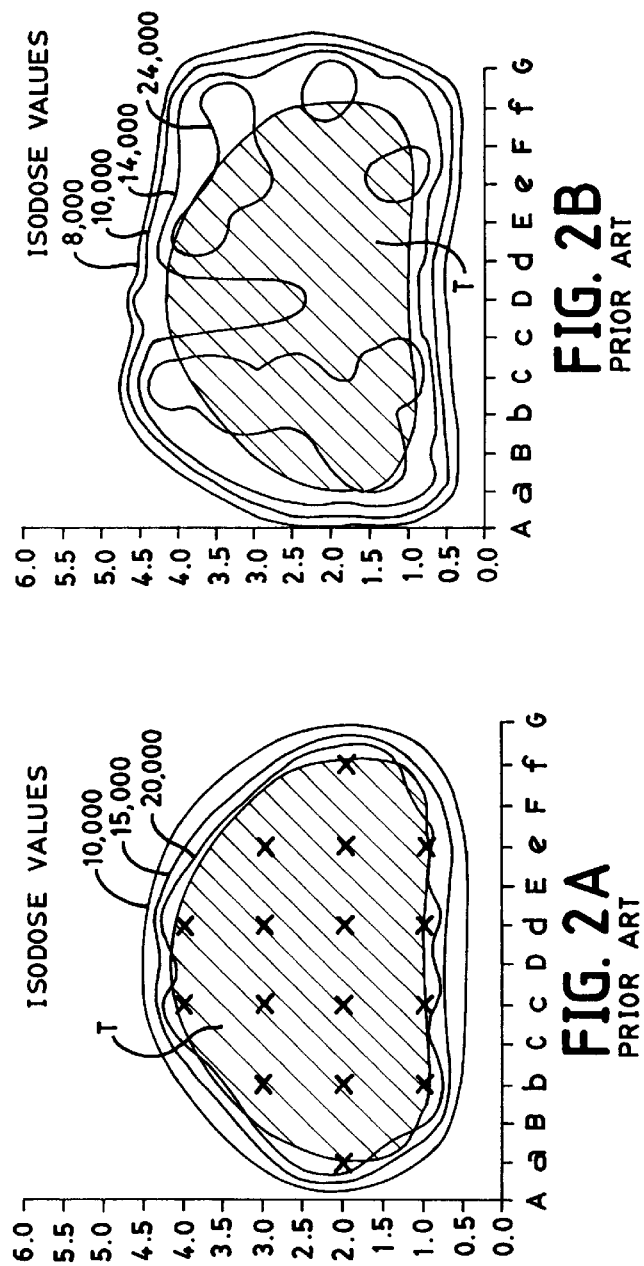
FIG. 2A
PRIOR ART
FIG. 2B
PRIOR ART

IMPLANTABLE RADIOTHERAPY DEVICE

TECHNICAL FIELD

The invention is directed to radiotherapy devices, and particularly to implantable radiotherapy devices which are adapted to deliver a predetermined dose of radiation in a predetermined pattern over a predetermined time period for the treatment of proliferative lesions, such as scar tissue and benign and malignant tumors.

BACKGROUND OF THE INVENTION

Tumors, stenoses of biological conduits, and other proliferative lesions can be effectively treated with radiation, which is known to inhibit cellular proliferation. The mechanism by which radiation prevents such proliferative cellular response is by preventing replication and migration of cells and by inducing programmed cell death (apoptosis).

Cells are variably susceptible to radiation, dependent on the types of cells and their proliferative status. Rapidly proliferating cells are generally more radiation-sensitive, whereas quiescent cells are more radiation-tolerant. High doses of radiation can kill all functions of even quiescent cells. Lower levels can merely lead to division delays, but the desirable effect of reproductive death is still obtained. In this case, the cell remains structurally intact but has lost its ability to proliferate, or divide indefinitely. It appears that low level radiation produces this desirable effect without causing tissue destruction or wasting (atrophy).

Traditional high-dose external beam radiation treatment, and prolonged low-dose radiation treatment (brachytherapy), are well-established therapies for the treatment of cancer, a malignant form of cellular proliferation. In particular, attention is currently being directed to the practical aspects of the use of brachytherapy. These aspects are, of course, particularly significant when radioactivity is involved. A disease site in a patient may be exposed to radiation from an external beam, either as a stand-alone procedure or in conjunction with an operative procedure. Alternatively, the radioactivity may be incorporated into an implantable device. In the first case, higher intensities of radiation are needed. As a result, other organs may be unnecessarily exposed to radiation, and safety, handling and logistics problems arise. In the second case, the implantable devices are typically quite expensive. In particular, if radioactivity is added to the device, the device may only be effective for radiotherapy during a relatively short period during which the radioactivity is provided at a useful (therapeutic) level. Depending on the radioisotope used, the decay time may be as short as hours, days or weeks.

The current state of the art brachytherapy for treatment of localized lesions such as tumors of, for example, the prostate, breast, brain, eye, liver, or spleen, employs radioactive, "sealed source" seeds. The term "sealed source", as used herein, means that radioisotopes incorporated into a device are integral with the device and cannot be dislodged or released from the host material of the device in the environment of usage. A typical sealed source seed includes a radiation source encapsulated within an impermeable, biocompatible capsule made of, for example, titanium, which is designed to prevent any leaching or release of the radioisotope. The seeds are approximately the size of a grain of rice (typically 0.81 mm in diameter by 4.5 mm long) and are implanted individually at a treatment site within and/or around a lesion, typically with a medium bore (18-gauge) delivery needle.

Disadvantages of the use of such seeds as radiotherapy devices include their nature as discrete, or point, sources of radiation, and the corresponding discrete nature of the dosages which they provide. In order to provide an effective radiation dose over an elongated or wide target area, the seeds should be uniformly and relatively closely spaced. The need to ensure accurate and precise placement of numerous individual radiation sources undesirably prolongs the exposure of the surgical team to radiation. Moreover, the use of discrete seeds requires an elaborate grid matrix for their proper placement. This requirement is labor-intensive, and therefore costly. In addition, the discrete nature of the seeds renders them more susceptible to migration from their intended locations, thereby subjecting portions of the lesion, the treatment site, and surrounding healthy tissue to over- or under-dosage, reducing the effectiveness and reliability of the therapy.

Other disadvantages exist in radioactive seed therapy. Relatively few radionuclides are suitable for use in sealed-source seeds, because of limited availability of radioisotopes with the necessary combination of half-life, penetration depth and activity, and geometry. In addition, the implantation of seeds generally requires a delivery needle with a sufficiently large bore to accommodate the seeds and may, in some cases, require an additional tubular delivery device. The use of a relatively large delivery needle during seeding may cause unnecessary trauma to the patient and displacement of the lesion during the procedure. Also, because of the risk of migration or dislodgement of the seeds, there is the risk that healthy tissues near or remote from the lesion site will be exposed to radiation from seeds which have become dislodged from their intended locations and possibly carried from the body within urine or other fluids.

In an attempt to accomplish a more even distribution of radioactive seeds in a longitudinal, or z, direction, the so-called "rapid strand" approach provides a bioabsorbable strand or suture onto which several radioactive seeds have been preassembled in a uniform spacing approximately 10 mm apart. Unfortunately, although the seed spacing along the strand can provide a somewhat more uniform longitudinal radiation dosage to the patient, the strand itself may not be sufficiently rigid to allow it to be properly and reliably installed at the treatment site without becoming jammed in the delivery needles. In addition, because the dosage is administered from seeds, the radiation dose provided thereby has the limitations previously discussed relating to the discrete nature of the seeds.

In the treatment of intraocular tumors, hemispherical ophthalmic plaques incorporating a radioactive material are sewn directly to the eyeball to provide a radiation dose to the intraocular tumor on the concave side of the plaque. In one type of plaque, manufactured by Bebig (Germany), a thin film of Ru-106 is encapsulated within two sheets of silver. The silver sheet on the concave side of the plaque is approximately 0.1 mm thick, and the sheet on the convex side is approximately 0.7 mm thick. The plaque has a total thickness of about 1 millimeter. Greater sheet thickness provides additional radiation shielding but adds to the thickness of the plaque, which increases the discomfort to the patient.

In another embodiment, radioactive seeds are attached to the concave side of the plaque in a grooved polymer liner. However, because the radioactive seeds are themselves relatively bulky, these plaques are relatively bulky and therefore uncomfortable for the patient. In addition, nonuniform dose distribution appears to be unavoidable with plaques into which seeds are inserted. It is critical to provide a minimum dosage to every part of a tumor so that it can be eradicated without risk of redevelopment. On the other hand, a radiation source which is too energetic may penetrate beyond the intended treatment region and undesirably expose the optic nerve, the lens, the brain, and other radiation-sensitive tissues and organs to radiation. Certain radionuclides are disadvantageous because they inherently deliver an excessive radiation dose to the sclera. Other undesirable radiation sources may include higher-energy gamma rays which may penetrate deeply into the tissues surrounding the eye and also pose a risk of overexposure to the surgical team. It is therefore difficult to provide the appropriate dosage to the patient using currently available intraocular plaques.

U.S. Pat. Nos. 5,607,442, 5,059,166 and 5,176,617 to Fischell et al. disclose the use of radioactive stents for use in the treatment and inhibition of stenoses in biological conduits. Irradiation of biological conduits from the inside is known to prevent or inhibit cellular proliferation after injury or trauma, such as angioplasty and other surgical procedures, to the tissue. A radioisotope is integrated into the material of the stent by coating, alloying, or ion implantation methods.

The radioactive stents disclosed in the Fischell et al. patents are substantially tubular mesh structures which emit radiation in a generally cylindrical radiation pattern about the stent. The radiation pattern is thus defined by the entire geometry of the stent and not the specific application for which the stent is used.

One problem associated with the radioactive stents of Fischell et al. is the relatively inefficient, and somewhat indiscriminate, distribution of radioisotope over the surface of the device. The lattice structure of the Fischell et al. stents is believed to be uniformly coated or treated with a radioisotope in order to render the structure radioactive. The omnidirectional nature of radiation emitted from a radioisotope-treated mesh is relatively nonuniform in its intensity and distribution, primarily because of the mesh geometry of the device. Irradiation of a surface produces a radiation pattern which extends in a direction normal to each treated surface. If the surface is a lattice or mesh, radiation may be emitted in all directions from each treated crosspiece of the lattice. In many cases a significant amount of radiation emitted from the device, such as, for example, radiation emitted inwardly toward the central axis of the stent, or between adjacent crosspieces of the lattice, may be unusable, or even potentially harmful to surrounding tissue, because of its open mesh geometry.

It would be an advancement in the art to provide a general purpose radiotherapy delivery device which provides a selectively controllable dose of radiation in a predetermined and discriminating radiation pattern, without the risks of over- and under-dosage attendant with the use of radioactive seeds, or the problems associated with indiscriminate radioisotope distribution over the mesh structure of the type suggested by the Fischell et al. patents.

OBJECTS OF THE INVENTION

An object of the present invention is to provide a general purpose radiotherapy device which can be used in a wide variety of radiation treatments and radiotherapy applications.

Another object of the present invention is to provide a radiotherapy device which obviates the disadvantages of the prior art radiotherapy seeds and encapsulated films.

Another object of the present invention is to provide a radiotherapy device which is capable of supplying either a substantially uniform or a selectively variable dose of radiation in a predetermined discriminating profile or pattern which is not a sole function of the geometry of the entire device.

Yet another object of the present invention is to provide a radiotherapy device which is relatively easily implanted at a treatment site in a patient, either permanently or for later removal, with minimum trauma to surrounding tissue and minimum radiation exposure to handlers, technicians and the surgical team.

And another object of the present invention is to provide a radiotherapy device which is not subject to migration or dislodgement from the site of implantation.

And another object of the present invention is to provide a general purpose radiotherapy device which incorporates a source of radiation directly into the material of the device, thus forming a substantially sealed radiation source, without the need for encapsulation of either the radiation source or the device.

SUMMARY OF THE INVENTION

The radiotherapy device of the present invention provides an effective alternative to radiation therapy employing encapsulated radioactive seeds or films. The unitary structure of the radiotherapy device disclosed herein makes its implantation into a patient easier and less invasive than the implantation of radioactive seeds. The use of ion implantation technology to make the device renders the device reusable, thus greatly lowering its cost, and highly versatile as well. The device can be made in a variety of geometries, and radioisotopes can be implanted over all or only a portion of the device, so that it can be used in a wide variety of applications. Other advantages will be detailed more fully below.

According to the invention, there is provided a general purpose radiotherapy device for delivering a predetermined dose of radiation to a treatment site in a patient in a predetermined discriminating radiation pattern which can be, in some cases, substantially independent of the geometry of the entire device. The device comprises a biocompatible radiotherapy delivery vehicle, or template, which is adapted for implantation at a treatment site in a patient, and at least one source of radiation which is incorporated directly into at least a portion of the template to render that portion radioactive. The shape of the pattern of radiation emitted from the device (also referred to herein as the "radiation pattern") may be determined, for example, substantially by the distribution of the radiation source or sources over the exterior surfaces of the template and not solely by the shape or geometry of the entire template.

The device includes one or more radioisotopes which are incorporated directly into the material of at least a portion of the template using a technique selected from the group consisting of ion implantation, ion beam assisted deposition, sputtering, evaporation, laser ablation and plating.

In one embodiment, at least two different radioisotopes are incorporated into respective portions of the template. In another embodiment, at least two different radioisotopes are incorporated into the same portions of the template. In still another embodiment, a single radioisotope is incorporated into multiple portions of the template. In yet another embodiment, a single radioisotope is incorporated into the surface of substantially the entire template. In still another embodiment, there may be portions of the template which do not incorporate any radioisotope.

The template can be made of a shape-memory material which can be formed into a desired configuration, prior to implantation or in situ, upon exposure to one or more environmental conditions.

In one aspect of the invention, the template is in the form of a substantially elongated filament which extends along a principal axis. Radiation is emitted from the filament in a substantially elongated radiation pattern which extends along, and radially about, its principal axis. Depending on the precise placement of the radioisotope over the surface of the template, the radiation pattern may follow the geometry of the template, or it may assume some other shape extending from at least a portion of the template. In this way the radiation pattern can be fashioned in accordance with a predetermined spatial distribution as a function of the particular application for the template, and not solely determined by the shape of the template.

The filament can be made of a metal or a nonmetal, such as a polymer or a glass fiber. In a preferred embodiment, the filament can be either substantially solid or tubular and has an aspect ratio of at least three to one. The filament may be formed into either a two-dimensional or a three-dimensional shape to facilitate anchoring of the device and/or to obtain a radiation pattern of a specific shape. In one preferred embodiment, the filament is formed in the shape of a coil. In other embodiments, the filament is formed in, for example, a serpentine or a zig-zag shape.

The radiotherapy device can further include a layer of a biocompatible encapsulating material deposited over the surface of the template after incorporation of the radiation source or sources into the template. If desired, a non-radioactive therapeutic agent can also be incorporated into or applied to at least a portion of the template for delivery of the agent to the treatment site with the radiation.

According to another aspect of the invention, the template comprises a sheet-like or planar plaque, which may be contoured, extending over a predetermined area and having a first surface and a second surface. One or more radioisotopes is incorporated into at least a portion of at least one of the surfaces of the plaque. In a preferred embodiment, the plaque is provided with a substantially spherically contoured shape, with one of the surfaces being convex and the other being concave. One or more radioisotopes preferably is incorporated into at least a portion of the concave surface of the plaque so as to provide a very well-defined predetermined radation pattern adapted specifically for the particular application for the device.

The device is adapted for either permanent or temporary attachment to a region of tissue to be treated and accordingly can include an anchor portion for securing the device to tissue in a region to be treated.

In one embodiment of the invention, the device includes a biocompatible, substantially solid template, which can be in the form of, for example, an elongated filament or a sheet-like plaque.

According to another aspect of the invention, there is provided a method of treatment of a localized lesion with a predetermined dose of radiation. According to the method, a biocompatible template adapted for implantation at a treatment site in a patient is provided. The template includes at least one source of radiation which is adapted for incorporation into at least a portion of the template to render that portion radioactive. The radiation source is incorporated into the template in accordance with a predetermined distribution so as to achieve a predetermined radiation pattern, the shape of which is determined at least in part by the distribution of the radiation source on the exterior surfaces of the template and not solely by the shape of the template. The device is then implanted into a patient at or near the treatment site.

According to still another aspect of the invention, there is provided a kit for delivering a predetermined dose of radiation in a predetermined discriminating radiation pattern to a treatment site in a patient. The kit comprises a radiotherapy device in the form of a substantially elongated filament, as previously described, and a syringe for implanting the device into the patient.

Depending on the radioisotope used, the therapeutically effective life of the device may be measured in days, weeks, months or years. Thus, the device is adapted for either substantially permanent or temporary implantation into a patient.

BRIEF DESCRIPTION OF THE DRAWINGS

The foregoing and other features and advantages of this invention will be better understood from the following detailed description taken with the accompanying drawings, in which:

FIG. 1 is a simplified schematic diagram of a radioactive seed as known in the art;

FIG. 2A is a schematic diagram of a planned isodose profile for radiation from prior art radioactive seeds;

FIG. 2B is a schematic diagram of the actual isodose profile obtained from the placement of seeds according to the planned seeding pattern illustrated in FIG. 2A;

DETAILED DESCRIPTION OF THE INVENTION

Figure 3A:
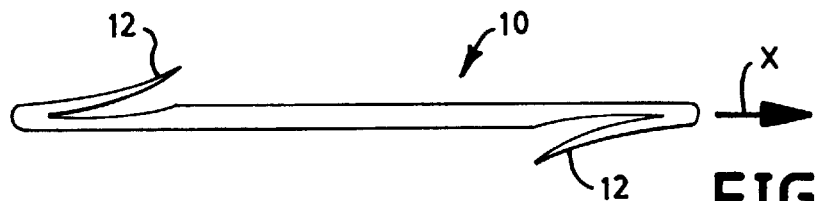
FIG. 3A is a side elevational view of an elongated radiotherapy device according to one aspect of the present invention.
Figure 3B:
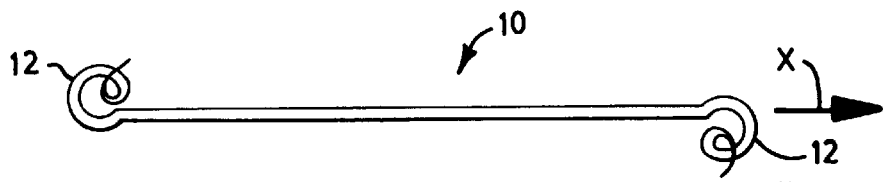
FIG. 3B is a side elevational view of an elongated radiotherapy device having a different type of anchor device at the ends of the device.

The invention is directed to the application of radionuclides directly into the surface of the material of an implantable, biocompatible template which can be of any geometry or shape which is suitable for the particular application. The radionuclides can be applied by various energetic physical vapor deposition (PVD) methods, such as, for example, ion implantation or ion beam assisted deposition. The distribution of radionuclides over the surface or surfaces of the template determines, at least in part, the shape and size of the radiation pattern which is obtainable from the device. Thus, the radiation pattern which can be obtained from the device is discriminating and is not limited to the shape of the entire template. The radiotherapy device of the present invention thus comprises a general purpose, unitary, sealed-source radiation delivery device which is suitable for use in the radiation treatment of tumors and other radiation-sensitive lesions which may require a complex or individualized pattern of radiation for effective treatment.

The term "implantable", as used herein, means any device which can be surgically installed in a patient and left inside the patient for any length of time, regardless of whether the device is later removed. The term "template", as used herein, means a radiation delivery vehicle into which is incorporated one or more species of radioisotope in a predetermined way to provide a radiation dose in a predetermined discriminating pattern. Thus, the shape of the template is not necessarily the shape of the radiation pattern obtainable from it.

Two applications in which the radiotherapy device of the present invention are of particular interest are the treatment of prostate tumors, both benign and malignant, and the treatment of ophthalmic lesions, such as intraocular melanoma, retinoblastoma, and macular degeneration. Other applications which may also be suitable for treatment with the device of the present invention include the treatment of breast, spleen, liver and brain tumors, as well as other localized tumors.

For example, in the case of radiotherapy of prostate tumors, the radiotherapy device of the present invention may comprise a relatively thin, narrow, elongated member, such as a relatively fine-gauge filament, which can be inserted into or around the tumor. The filament can be substantially solid in cross-section, or it can be tubular. The radiation pattern from such a device is generally also narrow and elongated, although it can have any shape which can be provided from a variety of geometries of the filament or distributions of radionuclides over the surface of the filament.

In the case of radiotherapy of ophthalmic lesions, the radiotherapy device of the present invention may comprise a plaque having, for example, a substantially spherically contoured shape with a predetermined radius of curvature. Implantation of radioisotopes into the concave surface of the plaque will produce a radiation pattern which converges toward a focal point within the tissue to be treated. The implantation of radionuclides over only a portion of the surface of the plaque, accomplished with masking devices or the like, can also produce, for example, annular or sector-shaped radiation patterns.

As will be detailed more fully below, the selection and combination of radioisotopes, and their distribution by ion implantation over the surface of the device, can provide a wide variety of discriminating radiation patterns and doses which can be customized to meet particular radiation therapy requirements.

FIG. 1 illustrates a prior art radioactive seed, such as is manufactured by Theragenics Corporation (Norcross, Ga.). The radioactive seed comprises a laser-welded titanium tube which contains within it two graphite pellets plated with radioactive palladium ($^{103}$Pd). The pellets are separated by a radiopaque lead marker. The seeds are 0.81 mm in diameter by 4.5 mm long, approximately the size of a grain of rice. The seeds are implanted in a patient at a treatment site with relatively large (1.25 mm, or 18-gauge) delivery needles.

As previously mentioned, the use of discrete radioactive seeds to provide a suitable radiation dosage to the tissue of interest is a tedious and labor-intensive process which cannot be reliably controlled to a satisfactory extent. FIG. 2A illustrates an intended seeding pattern for administration of radiation to a prostate lesion, the "x"s indicating the intended locations of the radioactive seeds. The seeds are intended to be regularly and uniformly spaced apart to provide a uniform dose of radiation which is greatest in the center of the target area (20,000 units of radiation) and diminished by 50% at the periphery of the target area T (10,000 units).

FIG. 2B illustrates the actual isodose profile obtained after seeding according to the plan illustrated in FIG. 2A. The actual and intended isodose profiles differ significantly, as indicated by the isodose contour lines of FIG. 2B. Isolated pockets of overdosage (24,000 units) are found at various locations within the target area T, and the isodose value at the periphery of the lesion (8000 units) is less than the intended isodose value at that location (10,000 units). A substantial portion of the lesion is exposed to a radiation overdose relative to the planned dose, while other portions of the lesion receive less than the minimum intended dose of radiation. In addition, an x-ray inspection of the seeded tissue would almost certainly reveal a relatively random orientation of the individual seeds, an indication of lesion displacement upon implantation of the seeds therein. This random orientation of seeds contributes to nonuniformity of the radiation dosages.

FIGS. 3A–3I and 4A–4B illustrate a radiotherapy device according to two aspects of the present invention. The device shown in FIG. 3A comprises an elongated, flexible member 10 which can be implanted into a patient either permanently or temporarily. The elongated member 10 extends along a principal axis X and is preferably in the form of a drawn or extruded filament made of either a metal or a nonmetal. The filament preferably should have a sufficient rigidity to permit its installation into and ejection from a delivery needle of a suitable gauge, or directly into the tissue itself without a separate delivery vehicle. It preferably has sufficient flexibility and/or shape memory to permit it to be bent before or after use, or even in situ, to accommodate various lesion geometries and anchoring requirements, as needed. Typical metals which are suitable for use as the filament include, for example, alloys of titanium, platinum, tantalum, tungsten, rhodium, palladium, gold, iridium, nickel, and stainless steel. Typical nonmetals which can also be used include polymers and even glass.

The template can further include means, preferably in the form of one or more anchors 12, which facilitates fixation of the template in the host tissue so that the template remains in place after implantation for the duration of the radiation treatment, and possibly indefinitely. As illustrated in FIG. 3A, a template in the shape of an elongated flexible filament may include barbs or anchors 12 at one or both ends, or some other suitable location. The anchor 12 can have any shape, such as a hook, shown in FIG. 3A, or a coil, shown in FIG. 3B, which functions to anchor the device in tissue.

The elongated member 10 can be made to any length which is suitable for the application. For example, a preferred length for use in prostate tumor therapy is between about 10 and 60 mm, and a preferred diameter is about 0.20 mm.

Figure 3C:
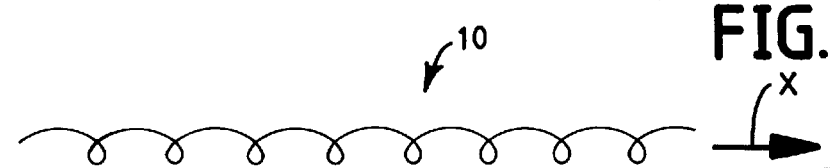
FIG. 3C is a side elevational view of an elongated radiotherapy device having a substantially coiled geometry.
Figure 3D:
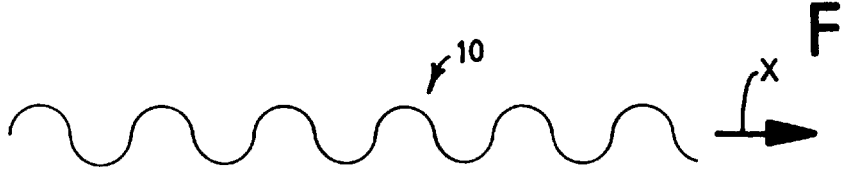
FIG. 3D is a side elevational view of an elongated radiotherapy device having a substantially serpentine geometry.
Figure 3E:
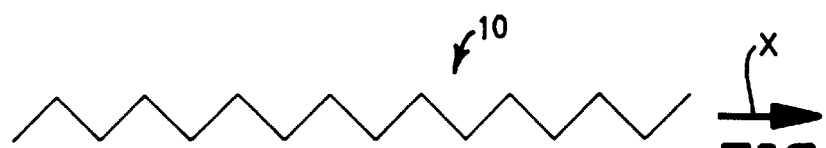
FIG. 3E is a side elevational view of an elongated radiotherapy device having a substantially zig-zag geometry.

As shown in FIGS. 3C–3E, the elongated member 10 can be made from a shape-memory material which is capable of being formed into a substantially two-dimensional or three-dimensional shape, either prior to implantation of the device in the patient, or even in situ, upon exposure to one or more environmental influences, such as, for example, heat, cold, humidity, salinity, pressure and acidity. The member can be formed, for example, into a zig-zag shape, or a helical or serpentine coil. The benefits of such a shaped device include enhanced fixation of the device in tissue, and the establishment of customized radiation fields or patterns around the device as a result of the proximity of radioactive portions of the device to one another. For example, in a coiled device formed from an elongated narrow filament which has been ion implanted with a single species of radioisotope over substantially its entire length, a relatively concentrated radiation dose is obtained in the region inside the coils of the device, whereas a relatively weak radiation dose is obtained in the region outside the coils. Other radiation dose profiles or patterns are obtainable by varying the density and distribution of radioisotope implantation into the implantable member and by varying the geometry of the template to obtain a desired discriminating radiation pattern shape.

Figure 3F:
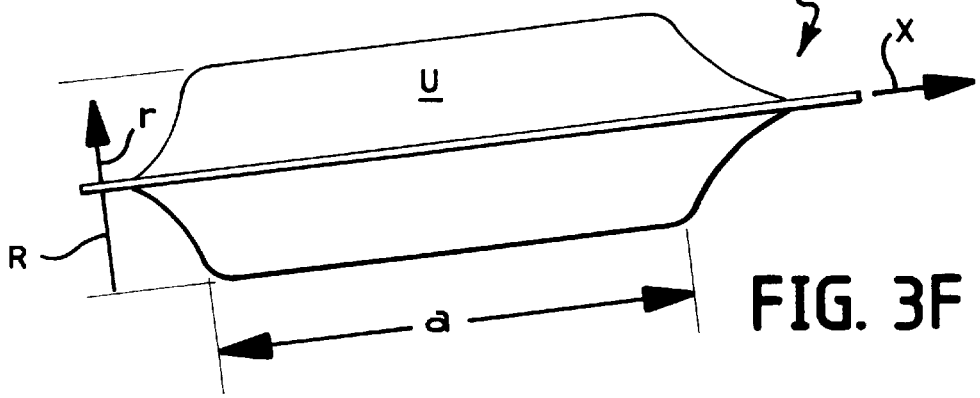
FIG. 3F is a perspective view of an elongated radiotherapy device having a substantially uniform radiation pattern extending along and about the device.
Figure 3G:
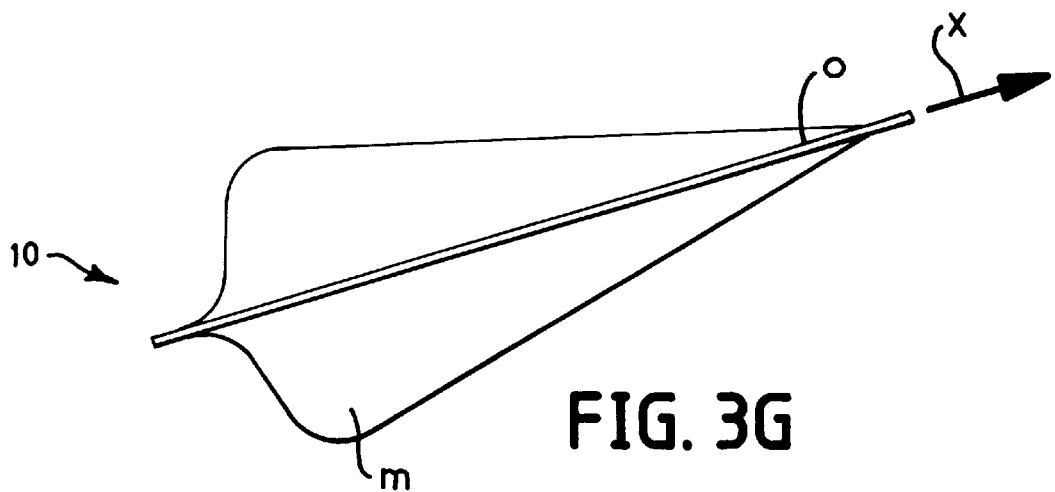
FIG. 3G is a perspective view of an elongated radiotherapy device showing a continuously varying radiation pattern extending along and about the device.
Figure 3H:
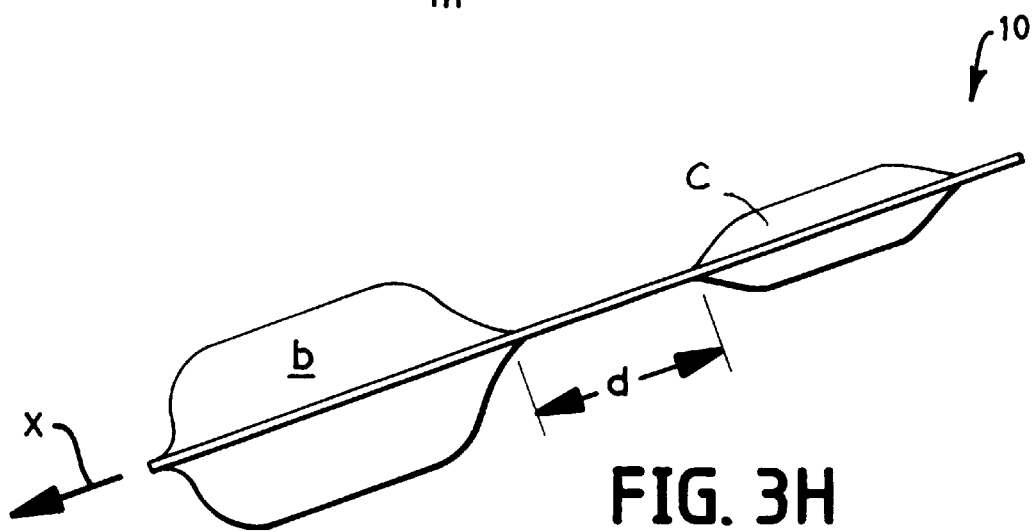
FIG. 3H is a perspective view of an elongated radiotherapy device showing several regions having different radiation pattern characteristics, as a result of selective ion-implantation of radionuclides over different portions of the device.

As shown in the detail view of FIG. 3F, one or more radioisotopes can be incorporated into the elongated member 10 by such energetic PVD methods as, for example, ion implantation, ion beam assisted deposition, sputtering, evaporation, laser ablation and plating. The distribution of radioisotopes over the surface of the member can provide, in one embodiment, a substantially uniform radiation dose U along, and extending about, the principal axis X of the member, as indicated in region a. The uniform radiation dose U extends radially out from the axis X and decreases in intensity with increasing distance r from the principal axis, until attenuated to some fraction of its intensity at some distance R. In another embodiment, the radiation dose can be tapered or otherwise continuously varied from some maximum value in one or more portions of the device to a minimum value in other portions of the device. For example, as illustrated in FIG. 3G, a radiation dose pattern may comprise a region of maximum dose M which tapers to a region of minimum dose O, such as near the ends of the implantable member. In still other embodiments, as illustrated in FIG. 3H, the radiation dose pattern can vary in either a regular or an irregular pattern, depending on the particular requirements for therapy in the region to be treated. This feature of the invention is highly advantageous in providing versatility and flexibility in treatment regimes for a wide variety of applications.

In one embodiment, shown in FIG. 3F, a single species of radioisotope is incorporated into substantially the entire length of the elongated member 10. As mentioned, this mode can provide either a substantially uniform radiation dose pattern, or a varying, discriminating pattern, depending on the implantation density and distribution of the radioisotope over the surface of the member. In another embodiment, two or more different species of radioisotopes can be incorporated into either respective portions of the surface of the member, such as in regions b and c, of FIG. 3H, or the same portions, illustrated at e in FIG. 3I, to provide a combination of radiation patterns. In addition, the elongated member 10 may include regions, such as region d in FIG. 3H, which have no radioisotope incorporated therein at all, so that substantially no radiation is provided to tissues in the region immediately surrounding that portion of the member.

Several radioactive elongated members can be implanted in a patient in and around a region of interest, such as a tumor or other localized lesion. The elongated members may be thin "micro"-filaments so that several can be used in a small target area or volume. Because of the substantially linear geometry of the elongated members, optimum dosage may typically be obtained with uniform radioactivity, i.e., uniform radioisotope emission, from the entire length of the member. In addition, all members implanted at a site are preferably identical in their radioactivity characteristics, and all members implanted at a site are preferably substantially straight, parallel and equally spaced from one another. The distances between the members are preferably identical in a given procedure but may vary from procedure to procedure.

The use of so-called radioactive "micro"-filaments for the treatment of proliferative tissue is an advancement over the current seeding techniques, as the radiation dosage obtainable using radioactive micro-filaments can be either substantially uniform over the entire length of the filament, or it can be selectively varied along the length of the filament. In any event, the dosage can be discriminately applied based upon the specific therapy requirements. In addition, the filaments can be positioned accurately and reliably, without migration or dislodgement of the radiation source from its intended position. Furthermore, the micro-filaments are preferably of a sufficient rigidity to permit them to be inserted into tissue, while being sufficiently flexible to permit them to be bent as needed, possibly even in situ, to accommodate a particular geometry and a desired radiation dose pattern.

The micro-filaments can be either substantially solid in cross-section, or tubular, or porous, or of any other geometry which facilitates the administration of a therapeutic dose of radiation in a discriminating predetermined radiation pattern. They can be cut to various lengths to suit the particular application, and they may be rendered radioactive over a portion or the entirety of their lengths, as needed.

The use of an elongated, thin, substantially solid, flexible member as the radiotherapy delivery vehicle, or template, is advantageous in facilitating precise placement of the device in the desired location and orientation relative to the lesion or lesions to be treated and in tailoring the radiation dosage to the treatment site. For example, one or more devices can be maneuvered to encircle a lesion or relatively consolidated group of lesions. Alternatively, several devices can be implanted to surround or penetrate a lesion or group of lesions. In addition, the longitudinal aspect of the device allows one or several radioisotopes to be incorporated therein in a predetermined linear or serial pattern, which may be determined by the size and nature of the lesion or lesions to be irradiated and the intended geometry of the micro-filament in situ. For example, as mentioned, a single radioisotope can be incorporated into a single elongated member over the entire length of the device. Alternatively, several different radioisotopes can be incorporated into several different segments of the member. Alternatively, irradiated segments of the member may be spaced apart from one another by segments which incorporate no radioisotope and are thus not radioactive. Such members can then be implanted into the tissue and oriented so that the ion implanted segments impinge on tissue to be treated while nonradioactive segments impinge on healthy tissue. Other variations of radioisotope incorporation and distribution which might be appropriate for a particular treatment regimen can be envisioned.

Figure 4A:
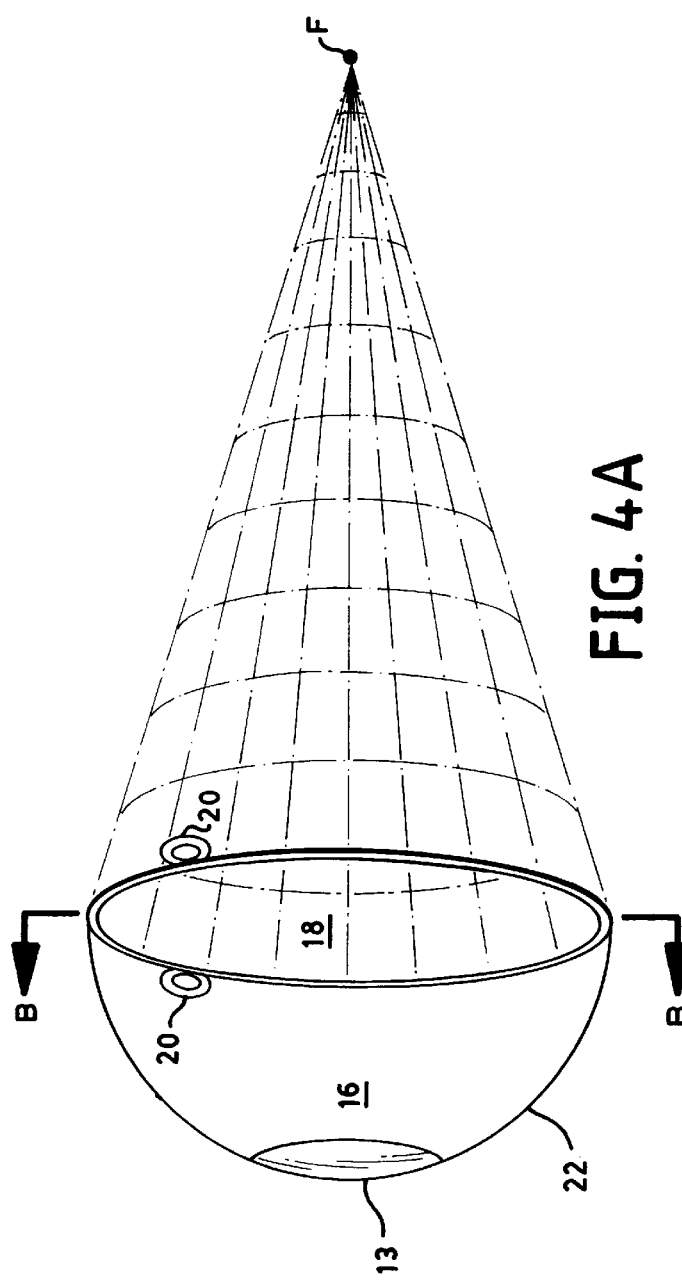
FIG. 4A is a perspective view of a radiotherapy device according to another aspect of the present invention, showing a radiation pattern which is obtainable by ion-implanting one or more radionuclides onto the concave surface of a hemispherical plaque.
Figure 4B:
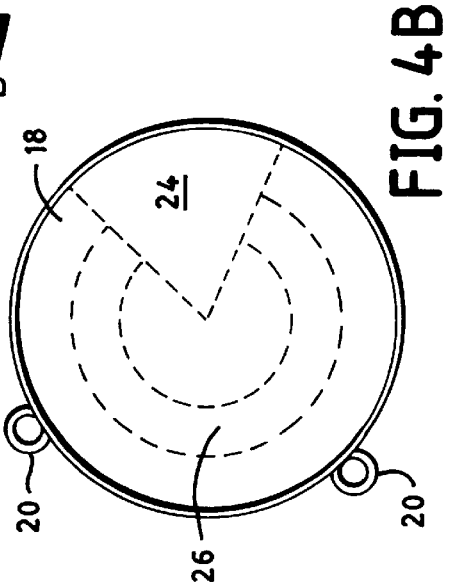
FIG. 4B is a frontal view of the radiotherapy device of FIG. 4A taken along lines B—B.

FIGS. 4A–4B illustrate a radiotherapy device according to another aspect of the invention. A planar brachytherapy source can comprise, for example, a planar or sheet-like ophthalmic plaque 14, into which are incorporated one or more radioisotopes. The plaque 14 may preferably be, in one embodiment, substantially spherically contoured or hemispherical in shape for use in treatment of lesions in the eye. A first surface 16 of the plaque is generally convex, and a second surface 18 is generally concave and complementary to the first surface, although the two surfaces need not correspond in shape. One or more species of radioisotope is incorporated into at least a portion of one or both surfaces of the plaque in order to provide a desired radiation dose in a desired radiation pattern. In a typical radiation pattern from an ophthalmic plaque into which a single radioisotope has been incorporated, the radioisotope is incorporated into the concave surface 18, so that radiation is emitted from that surface of the plaque in a conically converging pattern having a focal point F at a desired location, such as a tumor, within the interior of the eye. If desired, radioisotopes may also be integrated into the convex surface 16, so that radiation is emitted from that surface of the plaque in a conically diverging pattern. Other embodiments incorporating radioisotope over a portion of either or both surfaces are considered to be within the scope of the invention.

If desired, radioisotopes can be incorporated into various sectors 24 or annular rings 26 on a surface of the plaque, as shown in FIG. 4B, so that radiation is emitted from predetermined portions of the device in a predetermined pattern. Because radionuclides can be incorporated and integrated into selected portions of the template, the shape of the radiation pattern obtained from the device of the present invention is not governed strictly by the shape of the template.

As mentioned previously in connection with the elongated member embodiment, the plaque 14 includes one or more eyelets or other anchor means 20 for attaching the plaque to a region of tissue to be treated. Also, as previously mentioned in connection with the elongated member, the plaque can be either permanently attached to the eye, or it can be removed after the radiation therapy has been completed.

Figure 3I:
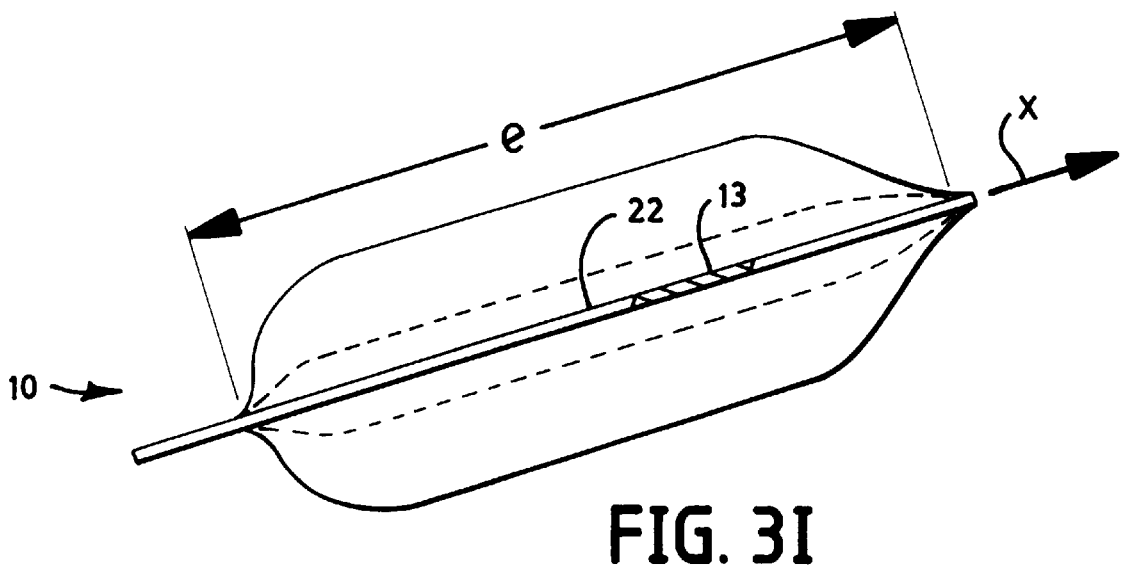
FIG. 3I is a perspective view of an elongated radiotherapy device having multiple radionuclides ion-implanted into the same portions of the device.

As shown in FIGS. 3I and 4A, it is possible to further enhance the sealed nature of the radioisotope-incorporated template by depositing a coating or layer 22 of a thin film of an encapsulating material, such as a polymer, metal or ceramic, which prevents leaching of any residual isotopic contamination or leaching of the template material. Typical techniques for obtaining the encapsulant coating include, for example, plating, sputtering, evaporation deposition, ion plating, plasma spray deposition, flame spray deposition, and chemical vapor deposition. Typical coating thicknesses may range from about 50 Angstroms to about 25 micrometers.

It may be also desirable to apply one or more non-radioactive therapeutic agents 13 over the surface of one or more portions of the templates, as shown, for example, in FIGS. 3I and 4A, in order to deliver both radiation and non-radiation treatments together. Such therapeutic agents can include, for example, chemical agents, thermal agents, biological agents such as proteins and growth factors, and other agents useful in various therapies. These agents can be applied either directly onto the radioactive template, or onto the encapsulant coating 22 over the radioactive template, as desired for the specific application.

The choice of material to be used for the template is not limited to any particular material. However, it is desirable to make the template substantially radio-opaque, or at least incorporate a radio-opaque marker or indicator into the material of the template, so that the template or marker can be seen in x-ray scans of the tissue being treated.

Figure 5:
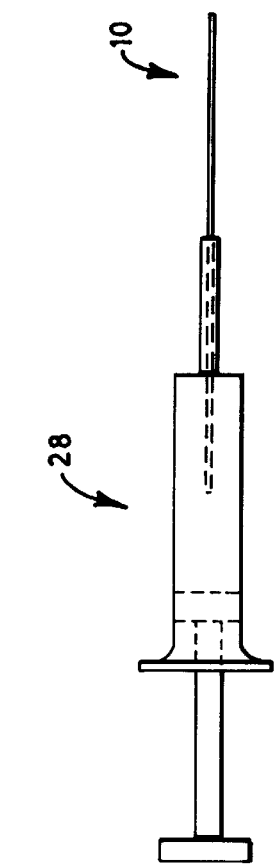
FIG. 5 is a side elevational view of a radiotherapy delivery kit according to the invention.

As shown in FIG. 5, a kit for delivering a predetermined dose of radiation in a predetermined discriminating radiation pattern to a treatment site in a patient includes a radiotherapy device in the form of a substantially elongated filament 10, as described herein, and a syringe 28 or like delivery vehicle for inserting the filament into the patient at or near the treatment site. The radiotherapy device is provided in a form which is suitable for the particular application, such as treatment of prostate tumors, and incorporates one or more radioisotopes which provide an appropriate radiation dose in an appropriate radiation pattern.

In the present invention, ion implantation techniques for incorporating the radioisotope into the template are especially preferred. In the ion implantation process, a filament in thermionic emission (with associated confinement) is used in an ion source to create a plasma. The positive ions produced in the plasma are extracted and accelerated in the presence of an electric field. A magnetic mass separator is used to select one particular isotope of an elemental species and deliver it to the work station, in which multiple devices to be treated are mounted. Finally, by using an electromagnetic focusing lens and raster scanning plates, the ion beam is focused and scanned onto the target, or substrate, material. The energetic ions impinge on the surface of interest and physically penetrate into the surface. The implanted species slow down by electronic and nuclear collision with the host surface atoms and eventually come to a stop as they are embedded in the host material. At the final rest position, the implanted species form chemical or physical bonds to the host atoms. Examples of chemical bonds include the formation of nitrides and carbides, while examples of physical bonds include the formation of alloys, which can be either ordered or amorphous. In either case, the incoming ion becomes an integral part of the surface, creating a sealed surface. Extensive research has borne out the mechanical and chemical stability of the ion implanted species in rather demanding tribological and corrosive environments.

The ion implantation technology used in the present invention provides for the incorporation of a known amount of a radioisotope into the surface of a radiotherapy delivery device template, such as, for example, a micro-filament or a planar or hemispheric plaque, and permits the radioisotope to be distributed over the surface of the template in a predetermined density so as to provide a predetermined dose of radiation in a predetermined delivery pattern.

The ability to select from among a wide variety of radioisotopes is critical. For optimum therapeutic results, the variables of radiation type, radiation field (depth of penetration) and intensity, half-life and biological activity all need to be selected with the therapeutic objective (e.g., cancer treatment), as well as the type of tissue, the extensiveness of the site to be treated, and the proximity of sensitive anatomy, in mind.

For example, for therapeutic indications involving only small localized sites, a beta emitter or a low-energy gamma ray emitter providing a relatively shallow penetration would be preferred. Candidates might include, for example, $^{45}Ca$, $^{123}Sn$, $^{89}Sr$, $^{32}P$, $^{33}P$, $^{103}Pd$, and $^{125}I$, although there other possibilities. For more extensive treatment areas, such as cancerous lesions, more deeply penetrating radiation is appropriate, such as from the gamma ray emitters $^{192}Ir$, $^{137}Cs$, $^{57}Co$ and $^{60}Co$. Additionally, the most appropriate radiation half-life may be dependent upon the type of treatment regimen required (i.e., chronic versus acute).

For the treatment of, for example, tumors of the prostate, it is preferred to employ a gamma/x-ray emitting radioisotope in the ion source and ion implant the radioisotope directly into a micro-filament to be used in treatment of the tumor. $^{125}$I and $^{103}$Pd, have been primarily used, as their half-lives (60 days and 17, days, respectively) and photon energies (27–35 keV and 20.1–23 keV, respectively) are known to be suitable for providing an appropriate dose of radiation to tumors of various sizes. In particular, $^{103}$Pd is preferred because it has an appropriate combination of half-life and photon energy for focused delivery of radiation to tumors without damage to surrounding tissue and organs. This radioisotope is already used in radioactive seeds used to treat prostate tumors, and thus its behavior in, and suitability for, this application is well-documented. In a preferred embodiment, $^{103}$Pd is implanted into 20-, 40- and 60 mm micro-filament segments to establish a specific activity for each filament (activity per unit length) which corresponds to the discrete seed activity, or seed source strength, provided by this species in seed form.

In the case of implantation of $^{103}$Pd into flexible platinum micro-filaments, the palladium is alloyed into the platinum substrate at a depth of 10 to 100 nanometers below the surface, depending on the energy attained by the palladium ions, to provide a sealed source. Radionuclide-implanted micro-filaments can be repeatedly autoclaved, sterilized by gamma- or electron-beam irradiation or ethylene oxide without deleterious effect.

The use of ion implantation technology to implant radioisotopes into the surface of a delivery template provides several advantages, such as ease of manufacturability of the device and the ability of the template to be reprocessed with successive ion implantation treatments as needed without adversely affecting the structural integrity of the device. Many different radioisotope species can be implanted using the ion implantation process, and this provides great flexibility in treatment regimes.

The combination of ion implantation technology with a solid template geometry overcomes the problem of the relatively uncontrolled and inefficient emission of radiation from a lattice structure, as in the Fischell et al. radioactive stents.

An advantage of the use of ion implantation techniques with templates of, for example, planar geometry is the ability to provide a directional radiation pattern because of the plurality of surfaces involved. A template in the form of a plaque or sheet, into which one or more species of radioisotope is well-integrated into one surface only, may provide virtually no radiation dose from an opposing surface if the plaque is made from a radio-opaque material. This feature is particularly advantageous in protecting medical personnel from the effects of radiation exposure from the device.

One of the desirable features of ion implantation is that the process creates essentially no perturbation of the substrate mechanical properties. It is therefore possible to carry out the process repeatedly without degradation. This is extremely important, because it is obvious that many devices will, for a variety of reasons, not be used while still appropriately active. Such devices would preferably be returned to the principal manufacturing facility for reprocessing and ultimate reuse, so as to lessen substantially the problems associated with device disposal.

The advantages of a general purpose radiotherapy device as described herein are many. In addition to those already mentioned, they include, for example, the highly uniform or selectively variable or discriminating dosage of radiation that can be delivered from the device, as well as an enhanced degree of control over the dosage which can be delivered from the device. In addition, use of the radiotherapy device of the present invention significantly reduces the physician's and technician's exposure to radiation during implantation of the device into the patient. Further, the trauma to the patient is minimized: the surgical implantation procedure is greatly simplified and can be performed with smaller or, in some cases, no delivery needles. The displacement of the lesion to be treated is minimized as well by the use of this radiotherapy device. In addition, the risks of migration and dislodgement of the radiation source are substantially eliminated, thereby reducing trauma to the patient and ensuring that radiation dosages are delivered precisely to the desired tissue without affecting healthy tissue.

Although a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

We claim:

1. A general purpose radiotherapy device for delivering to a treatment site in a patient a predetermined dose of radiation in a predetermined radiation pattern, said device comprising:
   a. a template made of a biocompatible material and adapted for implantation into or near a localized lesion or tumor in a patient; and
   b. at least one source of radiation incorporated into at least a portion of the template to render said portion of the template radioactive and define a unitary, structurally non-supporting radiation delivery device,
   wherein the shape of said radiation pattern is determined at least in part by the distribution of said source of radiation on the exterior surfaces of said template and is not determined solely by the shape of the template.

2. A radiotherapy device according to claim 1, wherein said source of radiation comprises one or more radioisotopes which are incorporated directly into the material of said template by a technique selected from the group consisting of ion implantation, ion beam assisted deposition, sputtering, evaporation, laser ablation and plating.

3. A radiotherapy device according to claim 2, comprising at least two different radioisotopes incorporated into respective different portions of said template.

4. A radiotherapy device according to claim 2, comprising at least two different radioisotopes incorporated into a single portion of said template.

5. A radiotherapy device according to claim 2, comprising a single radioisotope incorporated into one or more portions of said template..

6. A radiotherapy device according to claim 5, wherein said single radioisotope is incorporated into substantially all portions of the template.

7. A radiotherapy device according to claim 2, further comprising a layer of a biocompatible encapsulating material deposited over the surface of said template after incorporation of said radiation source into said template.

8. A radiotherapy device according to claim 2, further comprising a non-radioactive therapeutic agent applied to at least a portion of said template for delivery of said therapeutic agent to said localized lesion or tumor with said radiation.

9. A radiotherapy device according to claim 1, wherein said template is in the form of a substantially elongated flexible filament which extends along a principal axis, wherein radiation is emitted from said filament in a substantially elongated radiation pattern extending along and radially from said principal axis, wherein the filament is bendable in situ to accommodate various lesion geometries.

10. A radiotherapy device according to claim 9, wherein said filament is made of a metal.

11. A radiotherapy device according to claim 9, wherein said filament has an aspect ratio of at least 3 to 1.

12. A radiotherapy device according to claim 1, wherein said template is made of a shape-memory material which can be formed into a desired configuration, prior to implantation or in situ, upon exposure to one or more environmental conditions.

13. A radiotherapy device according to claim 1, wherein said filament is formed into a substantially three-dimensional shape.

14. A radiotherapy device according to claim 1, wherein said device is adapted for substantially permanent implantation in a patient.

15. A radiotherapy device according to claim 1, wherein said device is adapted for temporary or removable implantation in a patient.

16. A radiotherapy device according to claim 1, wherein at least a portion of said template emits substantially no radiation.

17. A radiotherapy device according to claim 1, wherein said template further includes anchoring means for securing said template in tissue at or near said localized lesion or tumor.

18. A general purpose radiotherapy device for delivering to a treatment site in a patient a predetermined dose of radiation in a predetermined radiation pattern, said device comprising:
  a. a template made of a biocompatible material and adapted for implantation at a treatment site in a patient; and
  b. at least one source of radiation incorporated into at least a portion of the template to render said portion of the template radioactive,
  wherein the shape of said radiation pattern is determined at least in part by the distribution of said source of radiation on the exterior surfaces of said template and is not determined solely by the shape of the template,
  wherein said template is in the form of a substantially elongated flexible filament which extends along a principal axis, wherein radiation is emitted from said filament in a substantially elongated radiation pattern extending along and radially from said principal axis, and
  wherein said filament is made of a nonmetal.

19. A radiotherapy device according to claim 18, wherein said filament is made of a polymer.

20. A general purpose radiotherapy device for delivering to a treatment site in a patient a predetermined dose of radiation in a predetermined radiation pattern, said device comprising:
  a. a biocompatible flexible filament adapted for implantation into or near a localized lesion or tumor in a patient, wherein the filament is bendable in situ to accommodate various lesion geometries; and
  b. at least one source of radiation incorporated into at least a portion of the filament to render said portion of the filament radioactive and define a unitary, structurally non-supporting radiotherapy delivery device.

21. A radiotherapy device according to claim 20, wherein said source of radiation comprises one or more radioisotopes which are incorporated directly into the material of said filament by a technique selected from the group consisting of ion implantation, ion beam assisted deposition, sputtering, evaporation, laser ablation and plating.

22. A radiotherapy device according to claim 21, comprising at least two different radioisotopes incorporated into respective different portions of said filament.

23. A radiotherapy device according to claim 21, comprising at least two different radioisotopes incorporated into a single portion of said filament.

24. A radiotherapy device according to claim 21, comprising a single radioisotope incorporated into one or more portions of said filament.

25. A radiotherapy device according to claim 24, wherein said single radioisotope is incorporated into substantially all of the filament.

26. A radiotherapy device according to claim 20, wherein said filament has an aspect ratio of at least 3 to 1 and extends along a principal axis, wherein radiation is emitted from said filament in a substantially elongated radiation pattern extending along and radially from said principal axis.

27. A radiotherapy device according to claim 20, wherein said filament is made of a flexible shape-memory material which can be formed into a desired configuration, prior to implantation or in situ, upon exposure to one or more environmental conditions.

28. A radiotherapy device according to claim 20, wherein said filament is made of a metal.

29. A radiotherapy device according to claim 20, wherein said filament is formed into a substantially three-dimensional shape.

30. A radiotherapy device according to claim 20, further comprising a layer of a biocompatible encapsulating material deposited over the surface of said filament after incorporation of said radiation source into said filament.

31. A radiotherapy device according to claim 30, further comprising a non-radioactive therapeutic agent applied to at least a portion of said filament for delivery of said therapeutic agent to said localized lesion or tumor with said radiation.

32. A radiotherapy device according to claim 20, wherein said device is adapted for substantially permanent implantation in a patient.

33. A radiotherapy device according to claim 20, wherein said device is adapted for temporary or removable implantation in a patient.

34. A radiotherapy device according to claim 20, wherein at least a portion of said filament emits substantially no radiation.

35. A radiotherapy device according to claim 20, wherein said filament further includes anchoring means for securing said filament in said localized lesion or tumor.

36. A general purpose radiotherapy device for delivering to a treatment site in a patient a predetermined dose of radiation in a predetermined radiation pattern, said device comprising:
  a. a filament made of a biocompatible material and adapted for implantation at or near a treatment site in a patient; and
  b. at least one source of radiation incorporated into at least a portion of the filament to render said portion of the filament radioactive, wherein said filament is made of a nonmetal.

37. A radiotherapy device according to claim 36, wherein said filament is made of a polymer.

38. A general purpose radiotherapy device for delivering to a treatment site in a patient a predetermined dose of radiation in a predetermined radiation pattern, said device comprising:

a. a biocompatible, substantially solid template adapted for implantation into or near a localized lesion or tumor in a patient; and b. at least one source of radiation incorporated into at least a portion of the template to render said portion of the template radioactive and define a unitary, structurally non-supporting radiotherapy delivery device, wherein the shape of said radiation pattern is determined at least in part by the distribution of said source of radiation on the exterior surfaces of said template and is not determined solely by the shape of said template.

39. A radiotherapy device according to claim 38, wherein said template is in the form of a substantially elongated flexible filament which extends along a principal axis, wherein radiation is emitted from said filament in a substantially elongated radiation pattern extending along and radially from said principal axis, wherein the filament is bendable in situ to accommodate various lesion geometries.

40. A method of treatment of a localized lesion with a predetermined dose of radiation, comprising the steps of:

a. providing a template made of a biocompatible material and adapted for implantation into or near a localized lesion or tumor in a patient, and at least one source of radiation adapted for incorporation into at least a portion of the template to render said portion of the template radioactive and define a unitary, structurally non-supporting radiotherapy delivery device, b. incorporating said radiation source into said template according to a predetermined distribution pattern, whereby the shape of the pattern of radiation provided by said device is determined at least in part by the distribution of said source of radiation on the exterior surfaces of said template and is not determined solely by the shape of said template; and c. implanting the device into or near a localized lesion or tumor in a patient.

41. The method of claim 40, wherein said radiation source is incorporated directly into the material of said template by a technique selected from the group consisting of ion implantation, ion beam assisted deposition, sputtering, evaporation, laser ablation and plating.

42. The method of claim 41, wherein at least two different radioisotopes are incorporated into respective different portions of said template.

43. The method of claim 41, wherein at least two different radioisotopes are incorporated into a single portion of said template.

44. The method of claim 41, wherein a single radioisotope is incorporated into one or more portions of said template.

45. The method of claim 44, wherein said single radioisotope is incorporated into substantially all of the template.

46. The method of claim 41, comprising the further step of depositing a layer of a biocompatible encapsulating material over the surface of said template after incorporation of said radiation source into said template.

47. The method of claim 46, comprising the further step of applying a non-radioactive therapeutic agent to at least a portion of said template for delivery of said therapeutic agent to said localized lesion or tumor with said radiation.

48. The method of claim 40, wherein said template is made of a shape-memory material which can be formed into a desired configuration, prior to implantation or in situ, upon exposure to one or more environmental conditions.

49. The method of claim 40, wherein said template is formed into a substantially elongated flexible filament having an aspect ratio of at least 3 to 1 and extending along a principal axis, wherein radiation is emitted from said filament in a substantially elongated radiation pattern extending along and radially from said principal axis.

50. The method of claim 49, wherein said filament is formed into a substantially three-dimensional shape.

51. The method of claim 40, comprising the further step of permanently implanting the device in a patient.

52. The method of claim 40, comprising the further step of removably implanting the device in a patient.

53. A kit for delivering to a treatment site in a patient a predetermined dose of radiation in a predetermined radiation pattern, the kit comprising:

a. a general purpose radiotherapy device, including a flexible filament made of a biocompatible material and adapted for implantation into or near a localized lesion or tumor in a patient, and at least one source of radiation incorporated into at least a portion of the filament to render said portion of the filament radioactive and define a unitary, structurally non-supporting radiotherapy delivery device, wherein the shape of said radiation pattern is determined at least in part by the distribution of said source of radiation on the exterior surfaces of said filament and is not determined solely by the shape of said filament, wherein the filament is bendable in situ to accommodate various lesion geometries; and b. a syringe for implanting the device into the patient.

54. A general purpose radiotherapy device for delivering to a treatment site in a patient a predetermined dose of radiation in a predetermined radiation pattern, said device comprising:

a. a template made of a biocompatible material and adapted for implantation at a treatment site in a patient; and b. at least one source of radiation incorporated into at least a portion of the template to render said portion of the template radioactive, wherein the shape of said radiation pattern is determined at least in part by the distribution of said source of radiation on the exterior surfaces of said template and is not determined solely by the shape of the template, wherein said template is made of a nonmetal.

55. A radiotherapy device according to claim 54, wherein said template is made of a polymer.

* * * * *